(12) United States Patent
Joseph (10) Patent No.: US 8,195,402 B2
(45) Date of Patent: Jun. 5, 2012

(54) METHOD AND AN APPARATUS FOR DETERMINING WELL OR FULLY DIFFERENTIATED MAMMAL CELLS

(75) Inventor: Heinz Walter Joseph, Frelburn (DE)

(73) Assignee: TETEC Tissue Engineering Technologies AG, Reutlingen (DE)

( * ) Notice: Subject to any disclaimer, the term of this patent is extended or adjusted under 35 U.S.C. 154(b) by 813 days.

(21) Appl. No.: 10/888,411

(22) Filed: Jul. 9, 2004

(65) Prior Publication Data

US 2006/0008795 A1    Jan. 12, 2006

(51) Int. Cl.
*G01N 33/48* (2006.01)
*G06F 19/00* (2011.01)
*G01N 31/00* (2006.01)

(52) U.S. Cl. ............................. 702/19; 702/20; 702/22

(58) Field of Classification Search .................. None
See application file for complete search history.

(56) References Cited

U.S. PATENT DOCUMENTS

| | | | |
|---|---|---|---|
| 6,054,262 A | 4/2000 | Hayakawa et al. | |
| 6,274,871 B1 | 8/2001 | Dukor et al. | |
| 6,493,080 B1 | 12/2002 | Boese | |
| 6,620,621 B1 | 9/2003 | Cohenford et al. | |
| 2005/0123917 A1 | 6/2005 | Labischinski et al. | |
| 2007/0003921 A1 | 1/2007 | Andrus | |
| 2008/0132418 A1 | 6/2008 | Ismail et al. | |

FOREIGN PATENT DOCUMENTS

| | | |
|---|---|---|
| DE | 199 49 953 A1 | 5/2001 |
| DE | 199 40 981 C1 | 7/2001 |
| DE | 100 60 560 A1 | 12/2001 |
| DE | 101 62 205 A1 | 7/2003 |
| DE | 101 62 960 A1 | 7/2003 |
| DE | 102 20 368 A1 | 12/2003 |
| DE | 102 22 896 A1 | 12/2003 |
| WO | WO 02/33400 A1 | 4/2002 |

OTHER PUBLICATIONS

Oberreuter et al. "Quantification of micro-organisms in binary mixed populations by Fourier transform infrared (FT-IR) spectroscopy" Letters in Applied Microbiology (2000) vol. 30, pp. 85-89.*

Erukhimovitch, V. "Spectroscopic characterization of human and mouse primary cells, cell lines and malignant cells", Photochem Photobiol (Oct. 2002) 76 (4) 446-51 (English Abstract Only).

Ami, D., et al., "Embryonic stem cell differentiation studied by FT-IR spectroscopy," *Biochim. Biophys. Acta 1783*:98-106, Elsevier Science Publishers, The Netherlands (2008).

Gué, M., et al., "Bacterial Swarming: A Biochemical Time-Resolved FTIR-ATR Study of *Proteus mirabilis* Swarm-Cell Differentiation," *Biochem. 40*: 11938-11945, American Chemical Society, United States (2001).

U.S. Appl. No. 12/560,290, inventor Joseph, H., filed Sep. 15, 2009.

Extended European Search Report for European Application No. EP 09 17 0329, filed on Jan. 12, 2009, European Patent Office, Germany.

English language Abstract of European Patent Publication No. DE 102 20 368 A1, EPO, espacenet database-worldwide (2003).

Office Action mailed on Dec. 23, 2010, in U.S. Appl. No. 12/560,290, Joseph et al., filed Sep. 15, 2009.

Office Action mailed on Sep. 8, 2011, in U.S. Appl. No. 12/560,290, Joseph et al, filed Sep. 15, 2009.

* cited by examiner

*Primary Examiner* — Eric S DeJong
(74) *Attorney, Agent, or Firm* — Sterne, Kessler, Goldstein & Fox P.L.L.C.

(57) ABSTRACT

A method and apparatus for the in vitro determination and typification of well-differentiated or fully differentiated mammalian cells is disclosed. The method comprises placing a cell sample on a sampling device, irradiating the cells with infrared light, preparing an FT-IR spectrum from the absorption spectrum, calculating derivatives of the FT-IR spectrum and comparing the derivatives to reference FT-IR spectra for known cell types. The apparatus comprises an infrared source and measuring apparatus capable of recording an absorption spectrum, and software for measurement, evaluation, documentation, and derivation of the absorption spectra. Fourier transformation he method is particularly useful for typing cells from tissue biopsies in preparation for cell transplantation.

20 Claims, 6 Drawing Sheets

METHOD AND AN APPARATUS FOR DETERMINING WELL OR FULLY DIFFERENTIATED MAMMAL CELLS

The present invention relates to a method the in-vitro determination of well or fully differentiated mammal cells, especially their qualitative determination and the typification, quantification, status analysis and/or status check of such mammal cells. In addition, the invention relates to an apparatus for carrying out this method.

BACKGROUND OF THE INVENTION

Methods for the determination, especially typification and status check of well or fully differentiated mammal cells are required especially in the field of transplantation medicine. For example, it is possible to produce replacement tissue by taking intact cells of the suitable tissue type from the recipient, cultivating them in vitro and re-introducing them into the patient after the necessary cell count has been reached. This can be effected either in the form of solutions or cultivated tissue portions or by cultivating the cells on a matrix (which preferably may be absorbed biologically) and re-implanting them together with the matrix. For example, suitable methods, matrices and cultivation media are described in the German applications 101 62 205.8, 101 62 960.5, 102 20 358.7, 102 22 896.5 and the literature cited therein.

Cultivation in vitro requires on the one hand that only the desired cell types are cultivated from any tissue biopsates obtained from the patient and, on the other hand, that only this cell type are transplanted into the patient. To achieve this, strict control of the preparation from the starting material, of the cell culture and of the finished cell product to be transplanted is necessary. An essential problem encountered both in the recovery of the biopsates and in culture management is the fact that cells in a tissue are not present in their pure form, but in the form of a mixture of different cell types. In addition to chondrocytes or cartilage cells, cartilage, for example, contains fibroblasts which are also found in most of the other tissues. Fibroblasts constitute an undesirable contamination of cell cultures insofar, as they usually grow faster than the desirable specific, well or fully differentiated cells. As a result, they can form the majority of the cells in the cultures after a very short time so that this culture no longer corresponds to the desired tissue type.

Until now, control of the transplants required the determination, especially typification and quantification, of the cells of this culture as well as the starting material and the finished product by means of morphological, histological and genetic methods (PCR). In addition to demanding substantial experience and knowledge on the part of the examiner, however, such determinations are very time-consuming and require sophisticated apparatuses to carry out the different tests. It would be desirable to have a simple method which, if possible, can be run automatically for the typification, optionally quantification and status check of the cells to be transplanted which permits rapid, routine and reliable determination.

SUMMARY OF THE INVENTION

The above-described problem is solved and other disadvantages of the prior art overcome by a method for the in-vitro determination, especially typification, of well or fully differentiated mammal cells comprising the steps of:
a) irradiating the cells with infrared light and recording the absorption spectrum obtained;
b) carrying out a Fourier transformation of the absorption spectrum from (a) to obtain an FT-IR spectrum;
c) calculating the first derivative and, optionally, higher derivatives of the FT-IR spectrum; and
d) comparing the derivative(s) from step (c) in a preselected wave number range with the same derivative(s) of reference FT-IR spectra determined earlier.

In addition to this method, a further subject matter of the invention is an apparatus for the in-vitro determination, especially typification, of well or fully differentiated mammal cells, comprising:
a) a sample-receiving device for a suspension of the well or fully differentiated mammal cells;
b) a means for irradiating the cells with infrared light and a means for recording the absorption spectrum obtained;
c) a means for carrying out a Fourier transformation of the absorption spectrum obtained into an FT-IR spectrum;
d) a means for calculating the first derivative and, optionally, further derivatives of the FT-IR spectrum; and
e) a means for comparing the derivative(s) from step (d) in a preselected wave number range with the same derivative(s) of reference FT-IR spectra prepared earlier and stored in the apparatus.

DESCRIPTION OF THE DRAWINGS

FIG. 6 shows how chondrocytes may also be classified with respect to their status. The ability to distinguish chondrocytes in buffer containing 10% of human serum albumin, 5% of human serum albumin or no serum albumin when examined immediately ex vivo is shown clearly. A comparison of FIG. 5 and FIG. 6 clearly shows the far lesser heterogeneity of the chondrocyte preparations among each other when compared to the heterogeneity between different cell types.

DETAILED DESCRIPTION OF THE INVENTION

The present invention relates to a method for the in-vitro determination of well or fully differentiated mammal cells which may be carried out in a simple and, preferably, automated manner, produces results rapidly and permits the reliable determination of well or fully differentiated mammal cells. For example, classical methods for the typification of cells such as morphological and histological methods and the genetic determination by means of PCR typically require up to 48 hours or longer until concrete results may be obtained. On the other hand, cells recovered when tissue samples are taken from a patient must be transferred into a culture immediately to keep the cells viable. Likewise, the transplant should be reintroduced into the patient as soon as possible, provided the desired cell count has been reached. In addition, typification of the cell material to be transplanted should be carried out within a short period of time before and as close to transplantation rather than at an interval of two days as was required under the prior art.

The method of the invention permits determination of the well or fully differentiated mammal cells—and particularly their typification—in a simple and reliable manner by irradiating the cells or an aliquot thereof with infrared light and recording the absorption spectrum obtained, carrying out a Fourier transformation on this absorption spectrum in order to obtain an FT-IR spectrum, calculating the first derivative and/or higher derivatives of the FT-IR spectrum and comparing said derivative(s) in a preselected wave number range with one or more derivative(s) of the same order of reference FT-IT spectra obtained earlier. The reference FT-IR spectra are generally obtained starting from preparations of purified, well or fully differentiated mammal cells of at least one cell type which preferably is the desired cell type. In case of cartilage transplants, for example, reference FT-IR spectra are obtained from purified preparations of chondrocytes. The derivatives of the FT-IR spectra of the transplant to be determined are then compared with the derivatives of this reference FT-IT spectrum.

Figure 1:
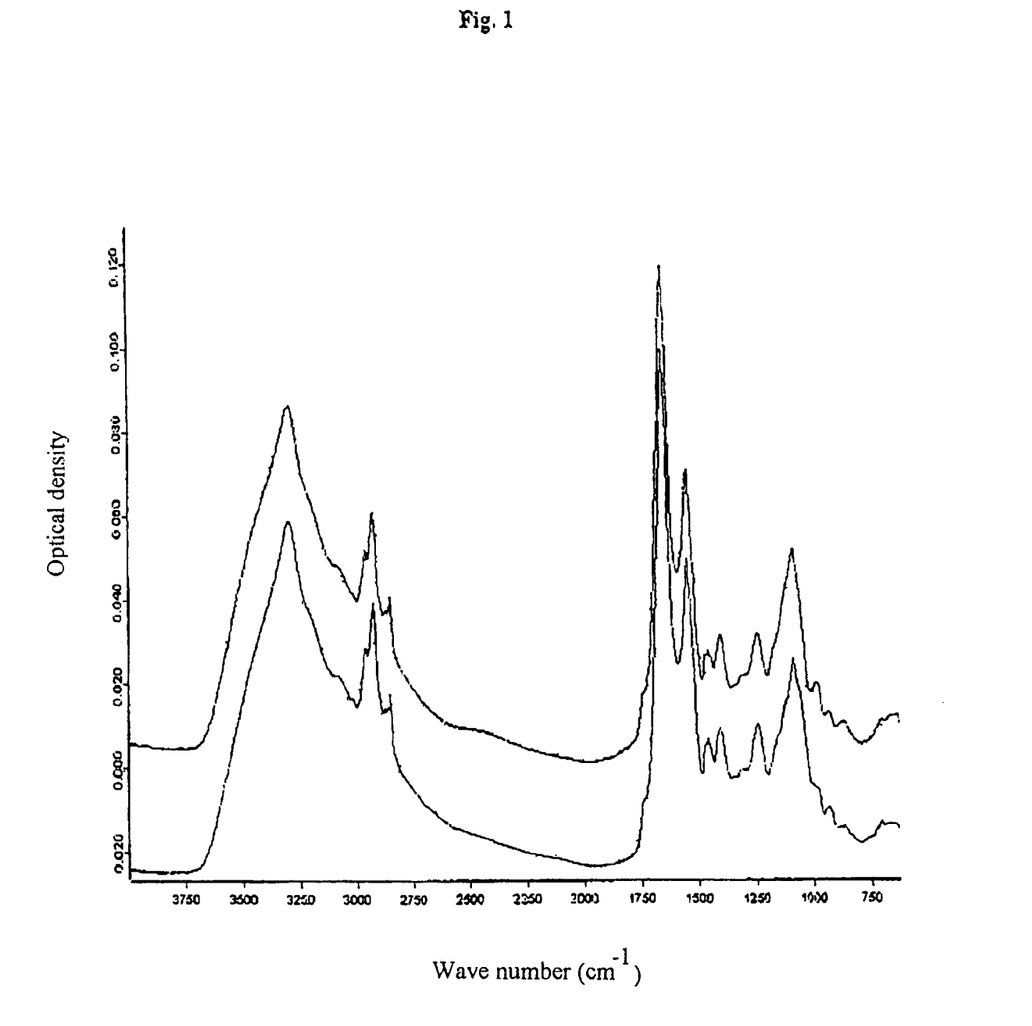
FIG. 1 shows an FT-IR spectrum of periosteal cells and chondrocytes in the wave number range between 700 and 4,000 cm$^{-1}$.
Figure 2:
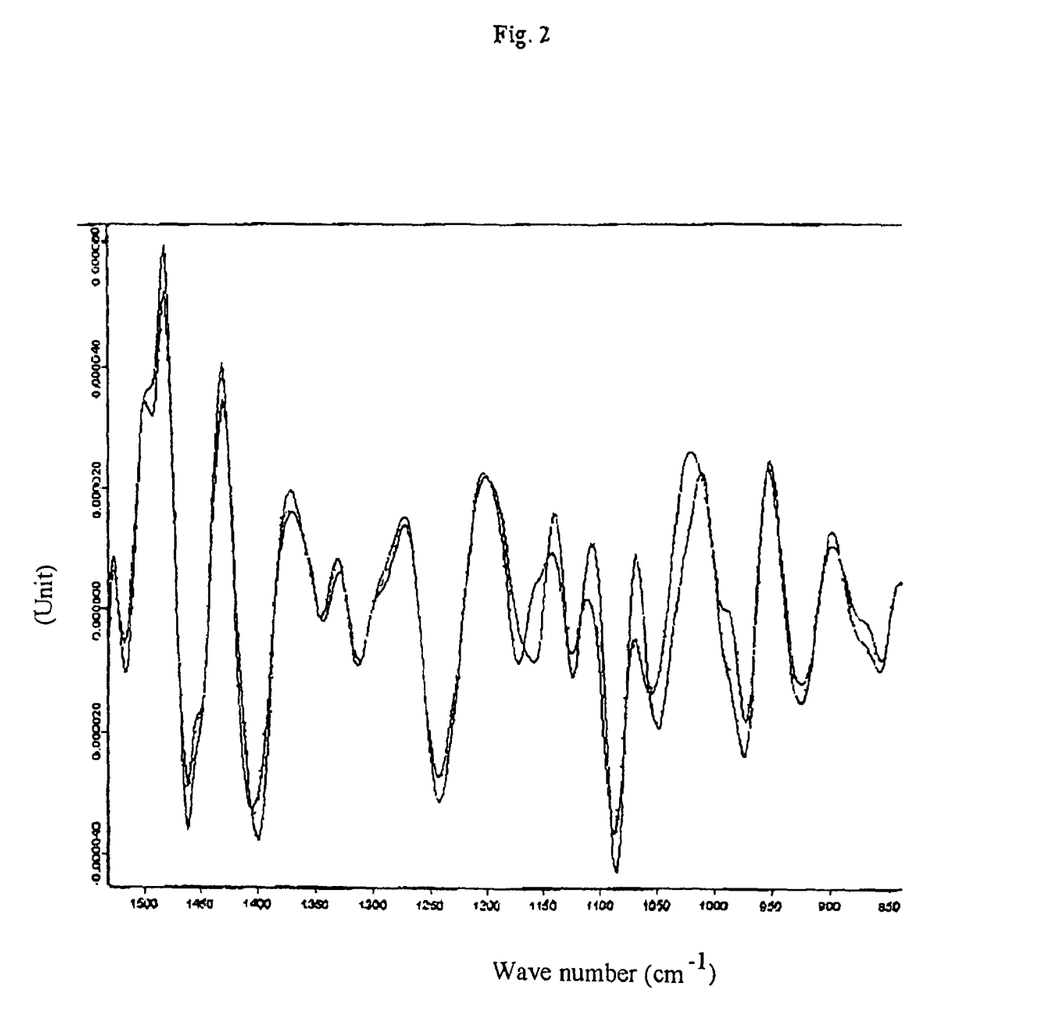
FIG. 2 shows the second derivative of the spectra from FIG. 1 in the wave number range from 900 to 1,200 cm$^{-1}$.

According to the invention, infrared light of a suitable wavelength is used to irradiate the cells. As a rule, any kind of infrared light may be used, i.e. light in the wavelength range from 760 nm to 500 μm. Infrared light of the near, medium or far IR range is suitable. Preferably, infrared light having a wavelength from 760 nm to 2,000 nm and most preferably infrared light of the medium range from 800 nm to 1,500 nm is used. The reason why the medium IR range is preferred is that a pronounced adsorption by carbohydrates may be observed. Without wishing to be bound by this theory, the inventor assumes that, in this range, the different carbohydrate structures are shown which, as is known, are expressed by each cell type on the cell surface. The comparison of the spectra of the carbohydrates therefore permits inference of the relevant cell type present in each case. FIG. 1 shows corresponding IR spectra of periosteal cells and chondrocytes for wave numbers in the range from 700 $cm^{-1}$ to 4,000 $cm^{-1}$. FIG. 1 also shows that there is no substantial difference of the FT-IR spectra of the cells themselves, but that, as shown in FIG. 2, the $2^{nd}$ derivatives display characteristic differences.

Accordingly, the invention uses the first derivation and/or one or more higher derivations of this spectrum for unambiguous differentiation. The $2^{nd}$ derivative of the FT-IR spectrum from FIG. 1 is shown for the range of the mean IR light in FIG. 2. FIG. 2 clearly shows that distinct and characteristic differences of the spectra are observed in the range of the second derivation and higher derivations even though there is considerable similarity of the actual spectra. These are used to determine the well or fully differentiated mammal cells in the invention.

Figure 3:
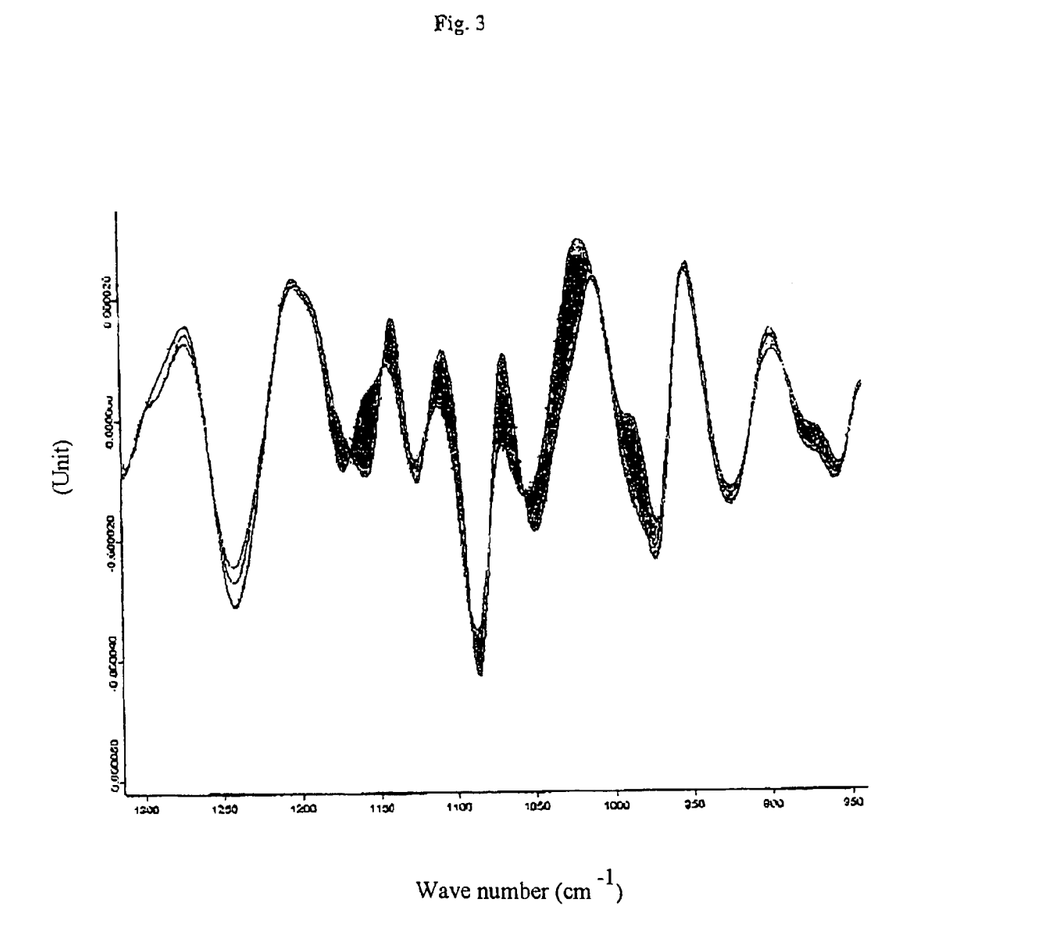
FIG. 3 shows the allocation of the characteristic differences of the spectra from FIG. 2 to individual cell groups by comparison with a standard.

FIG. 3 shows these second derivatives in comparison to a derivative of a standard chondrocyte preparation. The dark hatched areas show differences between chondrocytes and periosteal cells while the light hatched areas show differentiations among chondrocytes and the white difference areas represent periosteal cells. The heterogeneities of the spectra may be calculated by cluster analysis or differentiation and may be shown in the form of a so-called dendrogramme. Such dendrogrammes may be determined by known algorithms. For example, such algorithms are known from the manual of the software "Opus" Version 4.2, Spectroscopic Software by Bruker GmbH, the disclosure of which is included in this application by reference. The more similar these cells are, the lower is their heterogeneity. The heterogeneity of two cells can be inferred from the shortest connecting path in the dendrogramme.

Figure 4:
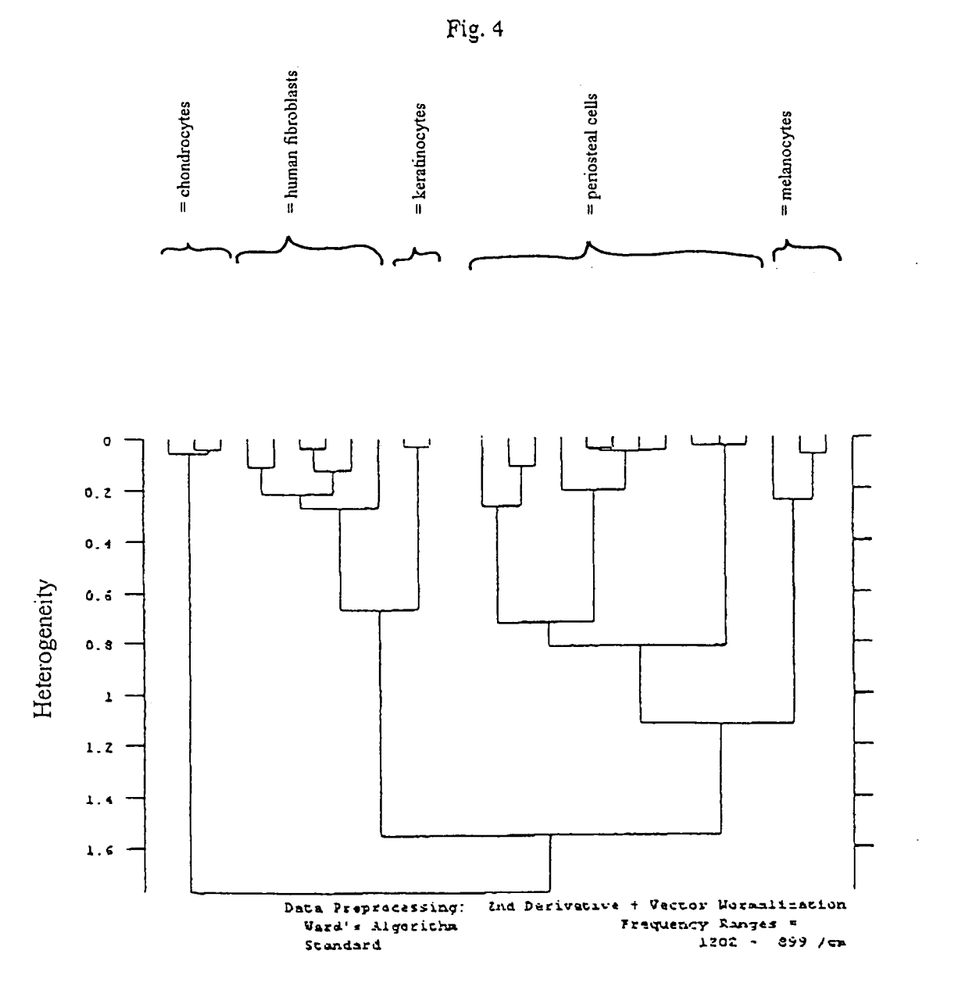
FIG. 4 shows a dendrogramme of the different cell types; the spectra of different samples were allocated to different families on the basis of their heterogeneity. This shows that an unambiguous allocation to a certain cell type can be achieved from the heterogeneity of the second derivations obtained according to FIG. 2.

FIG. 4 shows a dendrogramme for chondrocytes, human fibroblasts, keratinocytes, periosteal cells and melanocytes, with the result that the heterogeneity between chondrocytes and all other cell types is about 1.7, whereas the heterogeneity between human fibroblasts and keratinocytes is only about 0.7. The higher the heterogeneity is, the more safely the cell types may be distinguished from each other.

In order to improve the resolution, it is preferred to measure several samples of the same cell type processed in the same manner and to standardise the spectra obtained. Standardisation, Fourier transformation and derivation are carried by methods known to the person skilled in the art. Preferably all calculations are made by computer. In accordance with the invention, derivatives of the $2^{nd}$ and, optionally, a higher order may be used. Derivatives of the $2^{nd}$ order ($2^{nd}$ derivatives) are preferred.

Before step (a), the method according to the invention may additionally comprise:
(i) coating a suspension of the cells to be determined onto a suitable carrier;
(ii) evaporating the solvent from the suspension in order to obtain a dry sample.

As a rule, the method of the invention is carried out on cells in suspension. For this purpose, the cells may either be removed directly from the tissue formation and subjected to determination according to the invention. Alternatively, the cells may first be cultivated and aliquots of the culture examined by means of the method of the invention, optionally after trypsination for detaching the cultivated cells from their substrate. Optionally, aliquots of the sample solution may first be frozen and then thawed for testing. As a rule, 10 to 500 μl of the cell suspension at cell counts of $1\times10^3$ to $2\times10^5$ cells per ml are sufficient for the determination. The cells may be dissolved in a suitable solvent, such as water, culture medium, buffer, physiological saline, etc. It is not necessary to separate additives such as serum albumins, especially human serum etc., from this solvent.

The suspension is coated onto a carrier suitable for the IR measurement. After coating, the solvent is preferably evaporated so that a dry sample is obtained. According to the invention, this sample is irradiated with IR light and the adsorption spectrum recorded in accordance with the method of the invention. Preferably, at least three, generally three to five parallel measurements are taken on one sample. The carrier may consist of any material suitable for IR, preferably glass or silicon. For example, suitable carriers are described in the German patent application DE 100 60 560.

In step (d) of the method of the invention, the derivatives of the FT-IR spectra obtained from the sample are compared with the same derivative of a reference FT-IR spectrum obtained earlier. For this comparison, the reference spectra are obtained either starting from pure cultures of the cell type of interest and/or starting from known mixed cultures of the cell type of interest with one or more additional cell types. Preferably, the reference spectra are prepared starting from pure cultures of the cell type of interest in various solvents. One of these solvents is identical with the solvent of the sample.

Figure 5:
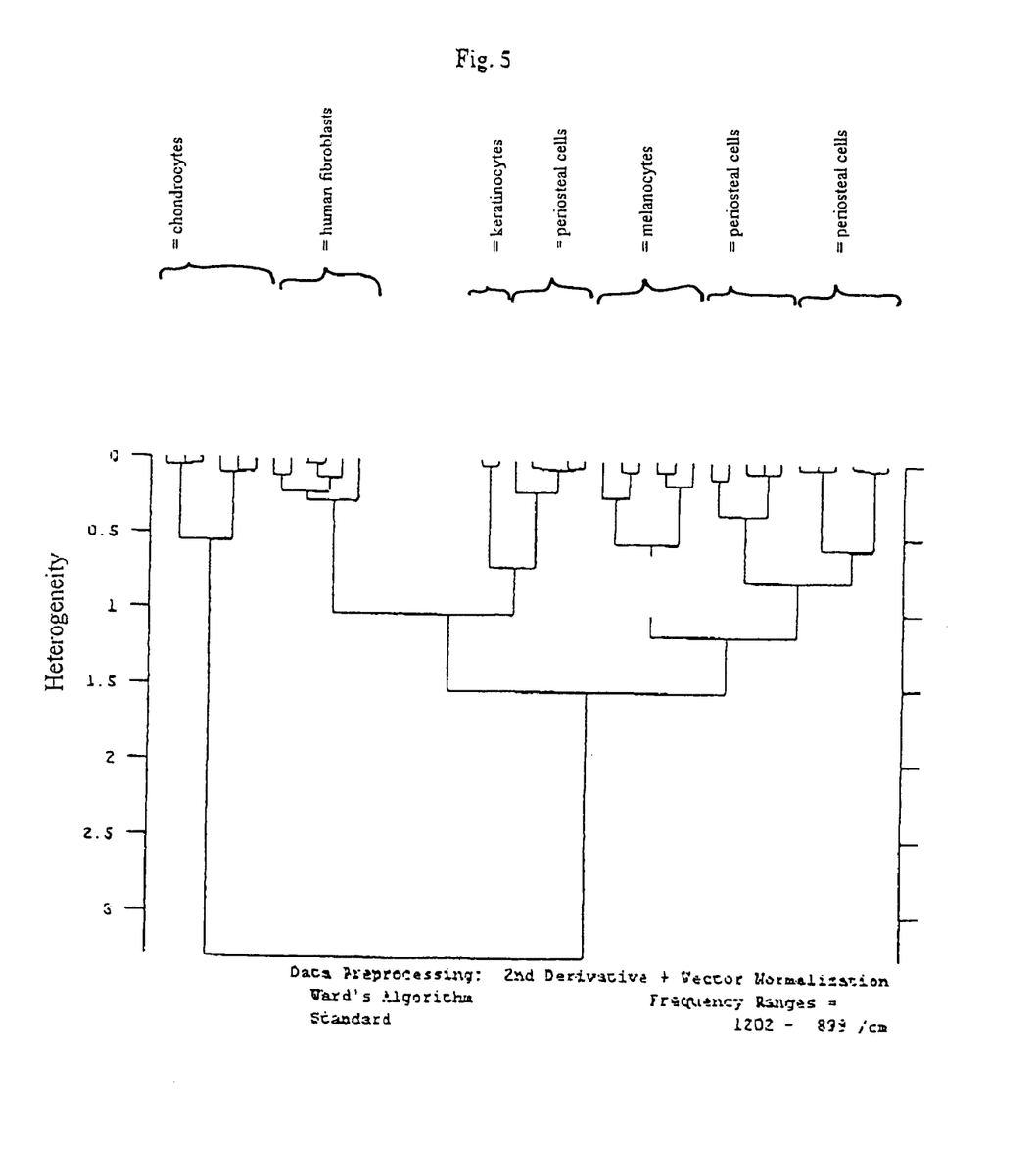
FIG. 5 shows the possibility of allocating blind samples to various cell types in accordance with the method of the present invention: D: chondrocytes; E: melanocytes; B and F: periosteal cells.

As FIG. 5 shows, varying the solvent makes it possible to determine the solvent environment of the cell type in question. For example, the method of the invention permits to distinguish suspensions of chondrocytes with 10% added human serum albumin from suspensions of the same cell type with only 5% added human serum albumin or those without serum albumin. Therefore, the invention permits not only determination of the cell type, but also a status check of the mammal cells concerning their environment.

If desired, the reference spectra may also be prepared starting from mixed cultures of the cell type of interest with one or more other cell types. Examples are mixed cultures of the desired cells and, for example, the ubiquitous contaminating fibroblasts. By a comparison with such mixed reference spectra, the method of the invention makes it possible to determine the contamination of a cell culture or sample and, optionally, the ratio between the desired cell type and the contaminating cell type.

The method of the invention permits the determination of well or fully differentiated mammal cells. Preferably, these are human tissue cells, especially connective tissue and supportive tissue cells. Most preferably the cells are selected from the group consisting of chondrocytes, osteocytes, periosteal cells and epithelial cells. In mixed cultures, fibroblasts are usually added as an additional cell type. The method of the invention may be used for qualitative determination, typification, quantification and/or as a status check.

The method of the invention is usually carried out in an apparatus for the in-vitro determination, especially typification, of well or fully differentiated mammal cells, comprising:
a) a sample-receiving device for a suspension of the well or fully differentiated mammal cells;
b) a means for irradiating the cells with infrared light and a means for recording the absorption spectrum obtained;
c) a means for carrying out a Fourier transformation of the absorption spectrum obtained into an FT-IR spectrum;
d) a means for calculating the first derivative and, optionally, further derivatives of the FT-IR spectrum; and
e) a means for comparing the derivative(s) from step (d) in a preselected wave number range with the same derivative(s) of reference FT-IR spectra prepared earlier and stored in the apparatus.

Apparatuses according to the features (a) to (d) are known in the prior art. In this respect, reference is made to the German patent specifications DE 199 49 953 or DE 199 40 981 the disclosures of which are included by reference. DE 199 49 953 relates to an Infrared Spectrometer and DE 199 40 981 relates to a Fourier Transform Infrared Spectrometer with an infrared measuring radiation source.

The apparatuses of the invention are characterised in that the reference spectra are already stored in the apparatus and an automatic comparison of the desired derivatives with the derivatives of the reference FT-IR spectra is therefore possible.

EXAMPLES

Example 1

An infrared measuring apparatus of the HTS-XT brand made by Bruker Optik GmbH, Germany, was used to carry out the method of the invention. This is an IR measuring apparatus for a standardised micro-titre plate format which already contains software for the measurement, evaluation— i.e. the Fourier transformation—and documentation as well as derivation of the absorption spectra recorded. Micro-titre plates of silicon permitting both transmission and reflection of the light were used for the measurements. The measurements were carried out with the following parameters: tensor 27; resolution 4 cm$^{-1}$; measurement time: 53 sec. per sample (64 scans).

3 to 4 µl of the cell suspension were coated onto the individual measuring points of the micro-titre plate; three parallel determinations were carried out for each sample.

The samples were frozen and subsequently thawed cell pellets of chondrocytes in PBS with and without 5 or 10 wt.-% of human serum albumin. These cell pellets were frozen with a cell count between $5 \times 10^5$ and $5 \times 10^6$ cells, stored at −20° C., thawed, shaken carefully and then applied directly. After coating, these suspensions were left to dry at room temperature for 30 minutes. The measurement was taken immediately after drying in a wavelength range from 700 to 4,000 nm (wave number 750 cm$^{-1}$ to 3,750 cm$^{-1}$).

The spectra obtained for periosteal cells and chondrocytes (without serum) are shown in FIG. 1. FIG. 2 shows the $2^{nd}$ derivative. Similar measurements were carried out on human fibroblasts, keratinocytes and melanocytes for typification of the different cell types in a wave number range from 900 cm$^{-1}$ to 1,200 cm$^{-1}$. The dendrogramme obtained is shown in FIG. 4.

Example 2

Using the dendrogrammes and spectra obtained in example 1 as reference spectra, blind samples subjected to the identical process were then examined. As shown in FIG. 5, it was possible to clearly allocate them to their pertinent cell type, namely chondrocytes, melanocytes and periosteal cells.

Example 3

In accordance with example 1, chondrocyte samples with 10% of human serum albumin and 5% of human serum albumin, without serum albumin as well as ex vivo samples, namely chondrocyte suspensions just prepared, i.e. without interim freezing, were examined.

Figure 6:
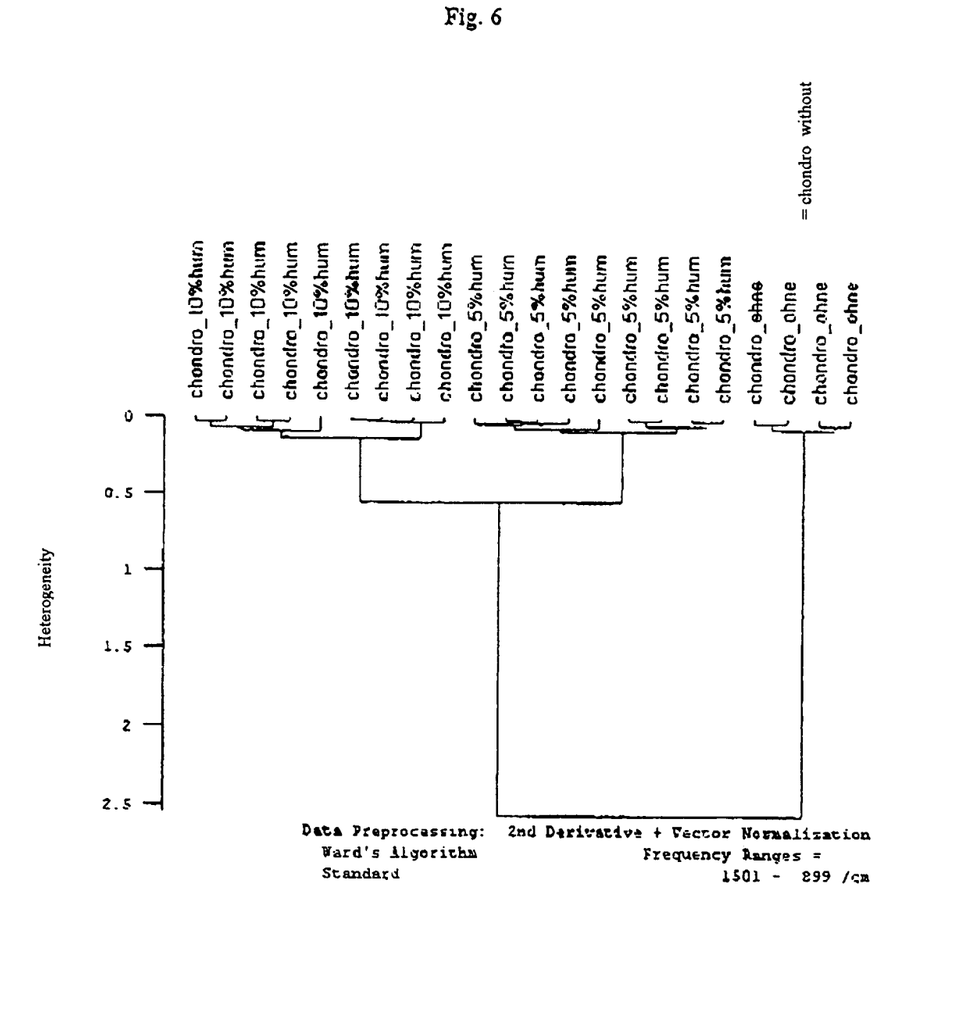

The corresponding dendrogramme is shown in FIG. 6. This dendrogramme shows that the method of the invention is also suitable for determining the status of the chondrocytes and their immediate solution environment.

Therefore, the invention provides a both simple and fast method for the determination, especially typification, of well or fully differentiated mammal cells which, for example, is suitable for routinely checking cell preparations used in transplantation medicine. One of the main reasons for that is that rapid, inexpensive typification is possible with minimum sample amounts.

The present invention is not limited to the subject matter of the samples shown above. A person skilled in the art will recognise that modifications of the method of the invention are possible without leaving the protective scope of the application defined by the appended claims.

The invention claimed is:

1. A method for determining or typifying in vitro well or fully differentiated mammal cells comprising the steps of:
a) irradiating the well or fully differentiated mammal cells with infrared light and recording the absorption spectrum obtained;
b) carrying out a Fourier transformation of the absorption spectrum from (a) to obtain an FT-IR spectrum;
c) calculating the first derivative and, optionally, higher derivatives of the FT-IR spectrum of the well or fully differentiated mammal cells using a computer program to calculate the first derivative and optionally higher derivatives of the FT-IR spectrum when the absorption spectrum from (b) is substantially similar to a underivatized reference FT-IR spectrum;

d) comparing the derivative(s) from step (c) in a preselected wave number range with the same derivative(s) of at least one reference FT-IR spectrum; and
e) displaying the result of the comparison of step (d); wherein the result indicates whether the cells are suitable for transplantation;
wherein the substantial similarity between spectra in step (c) is present when the well or fully differentiated cells and reference cells exhibit a heterogeneity of less than about 1.7, as determined by cluster analysis.

2. A method according to claim 1 wherein the reference FT-IR spectrum is obtained from preparations of purified well or fully differentiated mammal cells of at least one cell type.

3. A method according to claim 1 wherein the infrared light has a wavelength in the range of 760 nm to 500 μm.

4. A method according to claim 1 additionally comprising, before step (a), the following steps:
 (i) coating a suspension of the cells to be determined onto a suitable carrier;
 (ii) evaporating the solvent from the suspension in order to obtain a dry sample.

5. A method according to claim 1 wherein the reference spectrum for the comparison in step (c) is prepared from pure cultures of the cell type of interest and/or known mixed cultures of the cell type of interest with one or more additional cell types.

6. A method according to claim 5 wherein the reference spectrum is prepared from pure cultures of the cell type of interest in various solvents.

7. A method according to claim 1 wherein the reference spectrum is prepared from mixed cultures of the cell type of interest.

8. A method according to claim 7 wherein the determination is carried out on the basis of the second derivative of the FT-IR spectrum.

9. A method according to claim 5 wherein the mixed culture contains fibroblasts as an additional cell type.

10. A method according to claim 1 wherein the steps (a) to (d) are carried out automatically.

11. A method according to claim 1 carried out for the qualitative determination, typification, quantification and/or status verification of the mammal cells.

12. A method according to claim 1 wherein a heterogeneity value of various reference FT-IR spectra of different cell types is calculated from the comparison of the derivatives and typification is carried out by classification into a dendrogramme.

13. A method according to claim 1 wherein the infrared light has a wavelength in the range of 800 nm to 1,500 μm.

14. A method according to claim 7 wherein the mixed culture contains fibroblasts as an additional type cell.

15. A method according to claim 1 wherein the mammal cells are cells selected from the group consisting of chondrocytes, osteocytes, periosteal cells, epithelial cells, fibroblasts and muscle cells.

16. A method according to claim 1, wherein at least steps (a) to (d) are carried out by an infrared measuring apparatus.

17. A method for typifying well or fully differentiated mammal cells for transplantation, comprising:
 a) presenting a sample containing at least one differentiated mammalian cell type to an FT-IR spectrometer;
 b) irradiating the sample with infrared light and obtaining an FT-IR spectrum;
 c) calculating a second derivative of the FT-IR spectrum when the absorption spectrum from (b) is substantially similar to an underivatized reference FT-IR spectrum;
 d) conducting a comparison analysis between the second derivative calculated in step (c) and a reference second derivative;
 e) using the comparison analysis of step (d) to determine whether the population of cells for transplantation contain contaminating cell types; and
 f) identifying the population of cells for transplantation, wherein the substantial similarity between spectra in, step (c) is present when the well or fully differentiated cells and reference cells exhibit a heterogeneity of less than about 1.7, as determined by cluster analysis.

18. The method of claim 17, wherein the sample includes chondrocytes and fibroblasts, and wherein step (e) includes identifying presence of fibroblasts in the sample.

19. A method for determining or typifying in vitro well or fully differentiated mammal cells for transplantation, wherein the mammal cells are cells selected from the group consisting of chondrocytes, osteocytes, periosteal cells, epithelial cells and muscle cells, comprising the steps of:
 a) irradiating the cells with infrared light and recording the absorption spectrum obtained;
 b) carrying out a Fourier transformation of the absorption spectrum from (a) to obtain an FT-IR spectrum spectrum;
 c) calculating the first derivative and, optionally, higher derivatives of the FT-IR spectrum using a computer program to calculate the first derivative and optionally higher derivatives of the FT-IR spectrum when the absorption spectrum from (b) is substantially similar to an underivatized reference FT-IR spectrum;
 d) comparing the derivative(s) from step (c) in a preselected wave number range with the same derivative(s) of a reference FT-IR spectra; and,
 e) displaying the result of the comparison of step (d); wherein the result indicates whether the cells are suitable for transplantation,
 wherein the substantial similarity between spectra in step (c) is present when the well or fully differentiated cells and reference cells exhibit a heterogeneity of less than about 1.7, as determined by cluster analysis.

20. A method for determining or typifying in vitro well or fully differentiated mammal cells for transplantation, wherein the mammal cells are cells selected from the group consisting of one cell type and mixture of cell types, comprising the steps of:
 a) irradiating the cells with infrared light and recording the absorption spectrum obtained;
 b) carrying out a Fourier transformation of the absorption spectrum from (a) to obtain an FT-IR spectrum;
 c) calculating the first derivative and, optionally, higher derivatives of the FT-IR spectrum using a computer program to calculate the first derivative and optionally higher derivatives of the FT-IR spectrum when the absorption spectrum from b) is substantially similar to an underivatized reference FT-IR spectrum;
 d) comparing the derivative(s) from step (c) in a preselected wave number range with the same derivative(s) of a reference FT-IR spectra; and,
 e) displaying the result of the comparison of step (d); wherein the result indicates whether the cells are suitable for transplantation,
 wherein the substantial similarity between spectra in step (c) present when the well or fully differentiated cells and reference cells exhibit a heterogeneity of less than about 1.7, as determined by cluster analysis.

* * * * *